(12) United States Patent
Smith

(10) Patent No.: US 8,349,373 B1
(45) Date of Patent: Jan. 8, 2013

(54) DIETARY SUPPLEMENT FOR USE IN A WEIGHT LOSS PROGRAM

(76) Inventor: Conrad Anton Smith, Sandton (ZA)

( * ) Notice: Subject to any disclaimer, the term of this patent is extended or adjusted under 35 U.S.C. 154(b) by 0 days.

(21) Appl. No.: 13/189,821

(22) Filed: Jul. 25, 2011

(51) Int. Cl.
*A01N 65/00* (2009.01)
(52) U.S. Cl. ....................................... 424/725
(58) Field of Classification Search ......................... None
See application file for complete search history.

(56) References Cited

U.S. PATENT DOCUMENTS

2012/0114719 A1 * 5/2012 Morariu ........................ 424/401

* cited by examiner

*Primary Examiner* — Michael Meller
(74) *Attorney, Agent, or Firm* — Wenderoth, Lind & Ponack, L.L.P.

(57) ABSTRACT

This invention relates to a dietary supplement for use in a weight loss program, which alleviates insulin resistance in the presence of the metabolic syndrome. The dietary supplement includes, in combination, berberine, banaba leaf extract, and inositol. Also provided is a method of treatment in a weight loss program.

2 Claims, No Drawings

DIETARY SUPPLEMENT FOR USE IN A WEIGHT LOSS PROGRAM

BACKGROUND OF THE INVENTION

This invention relates to a dietary supplement for use in a weight loss program, which alleviates insulin resistance in the presence of the metabolic syndrome.

The metabolic syndrome, an increasingly common disorder associated with obesity, is a cluster of metabolic derangements that are associated with a significant increase in risk of cardiovascular disease. The syndrome is linked with primary disturbances in adipose tissue due to an excessive accumulation of visceral (intra-abdominal) fat in genetically susceptible individuals. The increased adipocyte mass assumes the role of an endocrine organ, communicating with other organ systems via a release of hormonal-like chemicals called inflammatory cytokines. The resulting disorders include insulin resistance and hyperlipidaemia (elevated blood cholesterol), hypertension and diabetes.

It is generally accepted that, for a diabetic, improved glycaemic control can lower cardiovascular risk. It has, however, also been demonstrated that in most cases diabetic medication, in particular the use of insulin, actually causes weight gain, often in individuals that are already overweight or obese. Clearly, iatrogenic (caused by medication) weight gain is not only unwelcome, but is also counterproductive. Limiting insulin-associated weight gain has therefore become a new treatment challenge.

Different strategies have been proposed to prevent or treat the development of obesity and the consequences of the metabolic syndrome. These include increased physical activity such as cardiovascular exercise for at least 30 minutes every day, and a healthy, calorie-reduced diet. There are studies that support the value of a healthy lifestyle, but it can be argued that these measures are effective in only a minority of people, primarily due to a lack of compliance with lifestyle and dietary changes.

Drug treatment is frequently required. Generally, the individual disorders such as hypertension, dyslipidaemia and diabetes that comprise the metabolic syndrome, are treated separately. In the absence of diabetes, however, the use of diabetic drugs for the treatment of insulin resistance in an overweight person is still controversial and, to the applicant's knowledge, no product has to date been approved by the Food and Drug Administration. Whilst insulin, the sulphonylureas and the thiazolidinediones are known to cause weight gain, metformin does not interfere with body mass and has therefore become a drug of choice.

Various studies have investigated the role that insulin plays in weight gain. In the United Kingdom Prospective Diabetes Study (UKPDS), for example, increased weight gain was directly related to improved glycaemic control and intensification of therapy with all pharmacotherapies, with the exception of metformin. However, weight gain was greatest in a group treated with insulin, where patients gained on average 6.5 kg. In addition, data from the Diabetes Control and Complication Trial (DCCT) demonstrated that insulin-associated weight gain was significantly greater in patients receiving intensified insulin intervention, as compared to conventional intervention.

Given that improved glycaemic control also improved the outcome of microvascular disease in the UKPDS and DCCT, it can be argued that the 'price' for improved glycaemic control against weight gain is a fair exchange. However, this historic argument makes a rather simplistic assumption when there is evidence that weight gain adversely affects cardiovascular risk. Excess adipose tissue is associated with increased levels of insulin resistance, which not only contributes to dyslipidaemia, but can also fuel a cycle of beta cell dysfunction, increased insulin resistance, a greater requirement for insulin and, ultimately, further weight gain. Besides potentially undermining the cardiovascular benefits of improved glycaemic control, weight gain is known to accelerate some disease processes that underlie diabetes. In this context, weight gain should be viewed as an undesirable side-effect of insulin and other obesity-promoting oral diabetic agents, making the use of insulin-sparing strategies an attractive option.

Insulin is an important controller of organic metabolism. It acts both directly and indirectly on most bodily tissues. Its actions can be divided into two broad categories:

a) its metabolic effects on carbohydrate, lipid, and protein synthesis; and b) its growth-promoting effects on DNA synthesis, mitosis and cell differentiation.

In general, metabolic effects occur almost immediately after a physiological rise in insulin concentration, whereas the growth-promoting effects require more time (hours and days) after exposure to elevated insulin concentrations to manifest themselves.

Insulin has several different effects that lead to fat accumulation in adipose tissue. Firstly, insulin promotes fat synthesis. When the quantity of glucose that enters the liver cells is more than what can be stored as glycogen, insulin promotes the conversion of excess glucose into fatty acids. These fatty acids are subsequently packaged as triglycerides in very low density lipoproteins and transported to the adipose tissue where they are deposited as fat. However, insulin also increases the utilisation of glucose by most of the body's tissues, which automatically decreases the utilisation of fat, thus functioning as a "fat sparer".

Secondly, insulin plays a role in fat storage. By inhibiting the action of hormone-sensitive lipase, an enzyme that causes hydrolysis of the triglycerides already stored in the fat cells, insulin inhibits the release of fatty acids into the circulating blood stream, thereby promoting obesity. Insulin also promotes glucose transport through the cell membrane into the fat cells in the same way that it promotes glucose transport into the muscle cells. Although some of this glucose is then utilized to synthesize small amounts of fatty acids, the glucose also forms large quantities of glycerophosphate which supplies the glycerol backbone that combines with fatty acids to form triglycerides molecules which are a dominant storage form of fat in adipose cells. Therefore, when insulin is not available, storage of a large amount of fatty acids transported from the liver via lipoproteins is almost totally blocked.

An object of the present invention is to provide a dietary supplement which, in a preferred embodiment, is intended to address at least some of the aforementioned factors.

SUMMARY OF THE INVENTION

The invention is based on the proposition that aspects of fat breakdown and use for providing energy are enhanced in the absence of insulin. This can occur normally between meals when secretion of insulin is minimal but the effect becomes extreme in diabetes mellitus when secretion of insulin is almost absent. When this happens, the aforementioned effects of insulin causing the production and storage of fat are reversed. A dominant effect is that the enzyme hormone-sensitive lipase in the fat cells become strongly activated. This causes hydrolysis of stored triglycerides, releasing large quantities of fatty acids and glycerol from the adipose tissue into the circulating blood. The net effect or result is significant weight-loss.

A goal in this respect is a strategy in which the insulin level is lowered to a value which is still healthy but which does not promote fat deposition and fat storage, thereby counteracting insulin's obesity promoting effects.

The invention consists of a combination of naturally derived compounds and plant extracts that display complementary and synergistic pharmaceutical effects, all of which have been proven to be useful for the treatment or alleviation of insulin resistance. The mode of action is via a triple-action mechanism, which optimises catabolic metabolism by lowering insulin levels and increasing the usage of fat for energy purposes, thereby assisting with weight loss.

The invention provides a dietary supplement which includes, in combination, berberine, banaba leaf and inositol.

The banaba leaf is derived from the banaba plant (*Lagerstroemia speciosa*).

The berberine and banaba leaf extract may be present in a ratio of from 1% to 300%.

The inositol may be present in a quantity of from 5% to 200% relative to the berberine.

The dietary supplement may include one or more of the following ingredients to enhance take-up, to act as a carrier for stabilisation purposes or for other reasons, as may be appropriate, namely chromium (in the form of amino acid chelate) calcium phosphate, corn starch, cellulose, silicon dioxide and magnesium stearate.

In a preferred embodiment the supplement was formulated as tablets, with each tablet including the following:

| | |
|---|---|
| berberine | 15 mg |
| banaba leaf extract | 420 mg |
| inositol | 30 mg |
| chromium | 75 mcg |

Individual dosage is 1-3 tablets once, twice or three times a day with meals.

Dosage can however be increased in more severe cases.

The composition per tablet may be in the following ranges:

| | |
|---|---|
| berberine | 5-100 mg |
| banaba leaf extract | 30-490 mg |
| inositol | 10-70 mg |
| chromium | 10-70 mcg |

DESCRIPTION OF PREFERRED EMBODIMENT

The dietary supplement of the invention is a combination agent indicated for the treatment of insulin resistance, obesity and metabolic syndrome. It contains three biological actives, namely berberine, banaba leaf extract and inositol.

Berberine is a quaternary ammonium salt from the group of isoquinoline alkaloids found in plants such as *Berberis, Hydrastis canadensis* and *Coptis chinenses*. Berberine has demonstrated the property of being able to up-regulate activity on both low-density-lipoprotein receptors (LDLR), as well as insulin receptors (InsR). To explain how this mechanism works, one has to touch on the topic of two common biological processes that happen throughout the body and to a large degree, control how the body communicates with cells. These processes are called 'downregulation' and 'upregulation'.

Each cell contains a certain amount of receptors on its surface membrane. The number of receptors can be increased ("upregulate") or decreased ("downregulated"). If a cell has fewer receptors on its surface membrane, it is less sensitive to a chemical messenger that is attempting to communicate with the cell. Examples of chemical messengers are hormones and neurotransmitters. Pharmaceutical drugs, however, or toxins, for that matter, may also occupy these receptors and act as chemical messengers.

An example of downregulation can be illustrated by the insulin receptor sites on the cells of a person with type 2 diabetes. If the number of receptors on the surface membrane decreases, the sensitivity of the membrane to insulin will also decrease. The body will compensate for this by releasing more insulin to complete the same task.

Insulin and LDL levels drop by up-regulating activity on low-density lipoprotein receptors (LDLR), responsible for LDL 'bad' cholesterol levels, and insulin receptors (InsR). This one-drug multiple-target characteristic makes berberine suited for the treatment of insulin resistance in the presence of the metabolic syndrome and obesity. Studies on berberine published in Pubmed demonstrate berberine's ability to stimulate glucose transport across the cell membrane to lower elevated blood glucose levels, to prevent or alleviate insulin resistance, to increase insulin receptor expression and to inhibit adipogenesis in human white preadipocytes. Trials have also demonstrated a unique tendency of berberine to lower elevated blood total cholesterol, LDL cholesterol and triglycerides, as well as atherogenic apolipoproteins (apo B)(Apo B).

Banaba (*Lagerstroemia speciosa*), also referred to as the Pride of India tree, is a medicinal plant that grows naturally in India, Southeast Asia and the Philippines. Tea brewed from the leaves is traditionally used to treat diabetes. The hypoglycaemic effect of banaba leaf extract has been shown to be similar to that of insulin. The blood sugar regulating properties of banaba and its ability to increase insulin sensitivity have scientifically been demonstrated in cell culture, animal and human studies. Tighter blood sugar control and a reduction in insulin levels have also demonstrated weight-loss in trials, even in the absence of dietary alterations.

Inositol occurs naturally as phytic acid in the fibre component of certain plant foods, and as myo-inositol in meat. It has an important role as a structural basis for numerous signalling and secondary messenger molecules that play a crucial role in a number of biological processes, including insulin signal transduction. Studies in patients with the polycystic ovary syndrome (PCOS), a condition known to be associated with insulin resistance and hyperinsulinemia, have demonstrated that inositol increases the action of insulin by improving insulin sensitivity. As a result, study subjects benefited by showing improved ovulatory function, decreased blood pressure and plasma triglyceride concentrations.

A dietary supplement, in accordance with the principles of the invention, was formulated in tablet form with the following composition per tablet:

| | |
|---|---|
| berberine | 15 mg |
| banaba leaf extract | 420 mg |
| inositol | 30 mg |
| chromium | 75 mcg |

The supplement was tested on a control group. The dosage regime was 1 to 3 tablets once, twice, or three times a day, with meals.

A trial based on the dosage regime, was conducted over a period of 25 days, using two groups, Group I and Group II, consisting of 7 and 15 subjects, respectively.

Group I was administered a placebo for the first 12 weeks of trial and thereafter for 13 weeks received the supplement. The following results were recorded:

TABLE 1

|  | GROUP I | |
| --- | --- | --- |
|  | Week 1-12 Placebo | Week 13-25 Supplement |
| participants | 7 | 7 |
| ave. weight lost per person (lbs) | 12.69 | 21.56 |
| ave. weight lost per person per week (lbs) | 1.06 | 1.66 |
| ave. BMI reduction per person (BMI) | 1.5 | 6.55 |
| ave. waist reduction per person (inches) | 0.5 | 1.5 |
| total cholesterol | 3% increase | 11% decrease |
| glucose | 5% decrease | 12% decrease |

The results in Table 1 indicate that the subjects from Group 1 had a higher average total and weekly, weight loss while on the supplement than on the placebo. The subjects had higher average BMI reduction and waist reduction measurements and a greater decrease in blood cholesterol and blood glucose content.

Group II was administered the supplement throughout the 25 weeks and the following results were recorded:

TABLE 2

|  | GROUP II | |
| --- | --- | --- |
|  | Week 1-12 Supplement | Week 13-25 Supplement |
| participants | 15 | 15 |
| ave. weight lost per person (lbs) | 24.5 | 23.9 |
| ave. weight lost per person per week (lbs) | 2.1 | 1.9 |
| ave. BMI reduction per person (BMI) | 7 | 6 |
| ave. waist reduction per person (inches) | 2.36 | 1.576 |

TABLE 2-continued

|  | GROUP II | |
| --- | --- | --- |
|  | Week 1-12 Supplement | Week 13-25 Supplement |
| total cholesterol | 15% decrease | 26% decrease |
| glucose | 9.8% decrease | 23% decrease |

The results from Table 2 show that the subjects had sustained high weight loss throughout the 25 week period. Total blood cholesterol and glucose content decreased substantially more in the final 13 weeks than in the first 12, indicating a decreased insulin resistance in the subjects.

The total weight loss, BMI and waist reduction measurements, and blood cholesterol and glucose content reduction for Group I and Group II were compared:

TABLE 3

|  | Total | Total |
| --- | --- | --- |
| Participants | 7 | 15 |
| ave weight lost per person (lbs) | 34.25 | 48.4 |
| ave weight lost per person per week (lbs) | 2.72 | 4 |
| ave BMI reduction per person (BMI) | 8.05 | 13 |
| ave waist reduction per person (inches) | 2 | 3.94 |

Table 3 shows a higher average weight loss and reduction in measurements (BMI and waist) in Group II than in Group I.

The supplement of the invention mimics the effect of insulin and improves the condition known as insulin resistance in which the effectiveness of insulin is lessened due to various biochemical reasons. As a consequence the body needs less insulin and therefore produces less. This results in a lower insulin level and facilitates weight loss.

The invention claimed is:

1. A composition for treating obesity in a patient in need thereof consisting essentially of therapeutically effective amounts of *hydrastis canadensis* extract, banaba leaf extract, inositol, and chromium.

2. A composition for treating obesity in a patient in need thereof consisting essentially of therapeutically effective amounts of *coptis chinensis* extract, banaba leaf extract, inositol, and chromium.

* * * * *